US009232804B2

(12) United States Patent
Woo et al.

(10) Patent No.: US 9,232,804 B2
(45) Date of Patent: Jan. 12, 2016

(54) COMPOSITIONS AND METHODS FOR STERILIZING BIOSCAFFOLDS

(71) Applicant: KNU University-Industry Cooperation Foundation, Chuncheon-si, Gangwon-do (KR)

(72) Inventors: Heung Myong Woo, Chuncheon-si (KR); Kyung Mee Park, Chuncheon-si (KR); Kamal El Din Hany Hussein, Chuncheon-si (KR)

(73) Assignee: KNU University-Industry Cooperation Foundation (KR)

( * ) Notice: Subject to any disclaimer, the term of this patent is extended or adjusted under 35 U.S.C. 154(b) by 203 days.

(21) Appl. No.: 14/112,722

(22) PCT Filed: Oct. 2, 2013

(86) PCT No.: PCT/KR2013/008818
§ 371 (c)(1),
(2) Date: Oct. 18, 2013

(87) PCT Pub. No.: WO2014/058175
PCT Pub. Date: Apr. 17, 2014

(65) Prior Publication Data
US 2015/0056302 A1    Feb. 26, 2015

(30) Foreign Application Priority Data

Oct. 11, 2012  (KR) .................. 10-2012-0113072
Oct. 11, 2012  (KR) .................. 10-2012-0113110

(51) Int. Cl.
*A01N 59/00*     (2006.01)
*A01N 1/00*      (2006.01)
*A01N 1/02*      (2006.01)

(52) U.S. Cl.
CPC *A01N 59/00* (2013.01); *A01N 1/00* (2013.01); *A01N 1/0231* (2013.01)

(58) Field of Classification Search
USPC ........... 422/20; 205/701; 424/600; 604/95.05
IPC ...................................... A01N 59/08
See application file for complete search history.

(56) References Cited

U.S. PATENT DOCUMENTS

2009/0202977 A1     8/2009  Ott et al.
2012/0156307 A1*    6/2012  Chen et al. .................... 424/600
2012/0302950 A1*   11/2012  Landsman et al. ......... 604/95.05

FOREIGN PATENT DOCUMENTS

| EP | 1588617 | * 10/2005 | ............. A01N 59/08 |
| JP | 10-081610 A | 3/1998 | |
| JP | 2001029435 A | 2/2001 | |
| KR | 100156000 B1 | 10/1998 | |

OTHER PUBLICATIONS

Brown et al., "The Basement Membrane Component of Biologic Scaffolds Derived from Extracellular Matrix," 12 (3):519-526 (2006).
Crapo et al., "An Overview of Tissue and Whole Organ Decellularization Processes," Biomaterials, 32:3233-3243 (2011).
De Villa et al., "Liver Transplantation for Hepatocellular Carcinoma in Asia," The Oncologist, 12:1321-1331 (2007).
Hodde et al, "Effects of Sterilization on an Extracellular Matrix Scaffold: Part II. Bioactivity and Matrix Interaction," Journal of Materials Science, 18:545-550 (2007).
Hoganson et al., "Preserved Extracellular Matrix Components and Retained Biological Activity in Decellularized Porcine Mesothelium," Biomaterials, 31:6934-6940 (2010).
Keane et al., "Consequences of Ineffective Decellularization of Biologic Scaffolds on the Host Response," Biomaterials, 33:1771-1781 (2012).
Lutolf et al., "Synthetic Biomaterials as Instructive Extracellular Microenvironments for Morphogenesis in Tissue Engineering," Nature Biotechnology, 23(1):47-55 (2005).
Ning et al., "Preparation and Characterization of Decellularized Tendon Slices for Tendon Tissue Engineering," Society for Biomaterials, 9 pages (2012).
Park et al., "Novel Method of Sterilization of Porcine Liver Bio-Scaffold Using Electrolyzed Water," The Transplantation Society, 24th International Congress of the Transplantation Society, Jul. 19, 2012 (1 page poster).
Punch et al., "Organ Donation and Utilization in the United States, 1996-2005," American Journal of Transplantation, 7(2):1327-1338 (2007).
Reing et al., "The Effects of Processing Methids Upon Mechanical and Biologic Properties of Porcine Dermal Extracellular Matrix Scaffolds," Biomaterials, 31:8626-8633 (2010).
Rosario et al., "Decellularization and Sterilization of Porcine Urinary Bladder Matrix for Tissue Engineering in Lower Urinary Tract," Regen Medical, 3(2):145-156 (2008).
Siritientong et al., "The Effect of Sterilization Methods on the Physical Properties of Silk Sericin Scaffolds," American Association of Pharmaceutical Scientists, 12(2):771-781 (2011).
Taylor et al., "Glycosaminoglycans and Their Proteoglycans: Host-Associated Molecular Patterns for Initiation and Modulation of Inflammation," The FASEB Journal Review, 20:9-22 (2006).
Uygun et al., "Organ Reengineering Through Development of a Transplantable Recellularized Liver Graft Using Decellularized Liver Matrix," Nature Medicine, 16(7):814-821 (2010).
International Search Report from corresponding PCT Application No. PCT/KR2013/008818 mailed Dec. 2, 2013 (5 pages).

* cited by examiner

*Primary Examiner* — Walter Webb
(74) *Attorney, Agent, or Firm* — Dardi & Herbert, PLLC; Curtis B. Herbert

(57) ABSTRACT

The present invention includes a composition for sterilizing a bioscaffold, comprising slightly acidic electrolyzed water (SAEW) as an active ingredient, and a method for sterilizing a bioscaffold using the same. The slightly acidic electrolyzed water according to the present invention has excellent effects on the sterilization of bioscaffolds and the removal of immunogenic antigens and a little effect on extracellular matrix, such as glycosaminoglycans or collagen. Moreover, the scaffold sterilized with the slightly acidic electrolyzed water has excellent cell attachment and has no toxicity, and thus the slightly acidic electrolyzed water can be effectively used for the sterilization of bioscaffolds.

5 Claims, 3 Drawing Sheets

Fig. 1
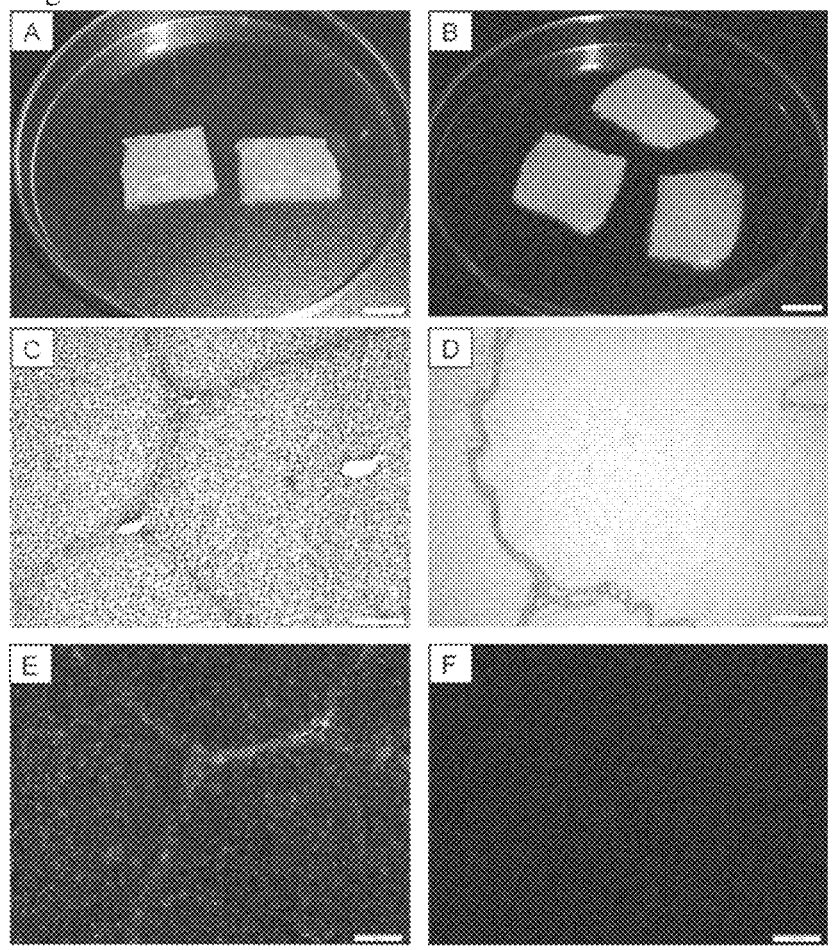
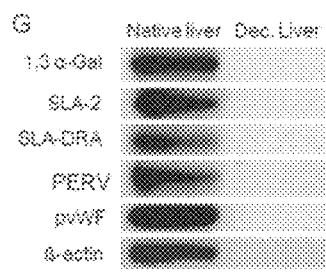
Fig. 2
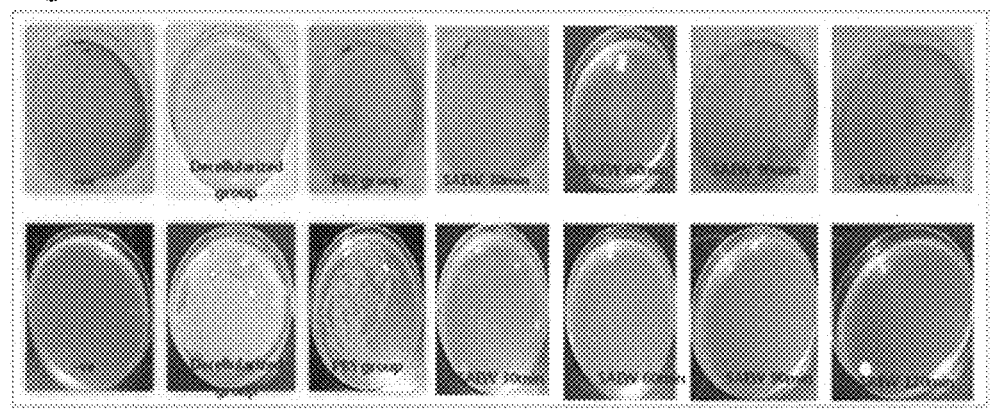

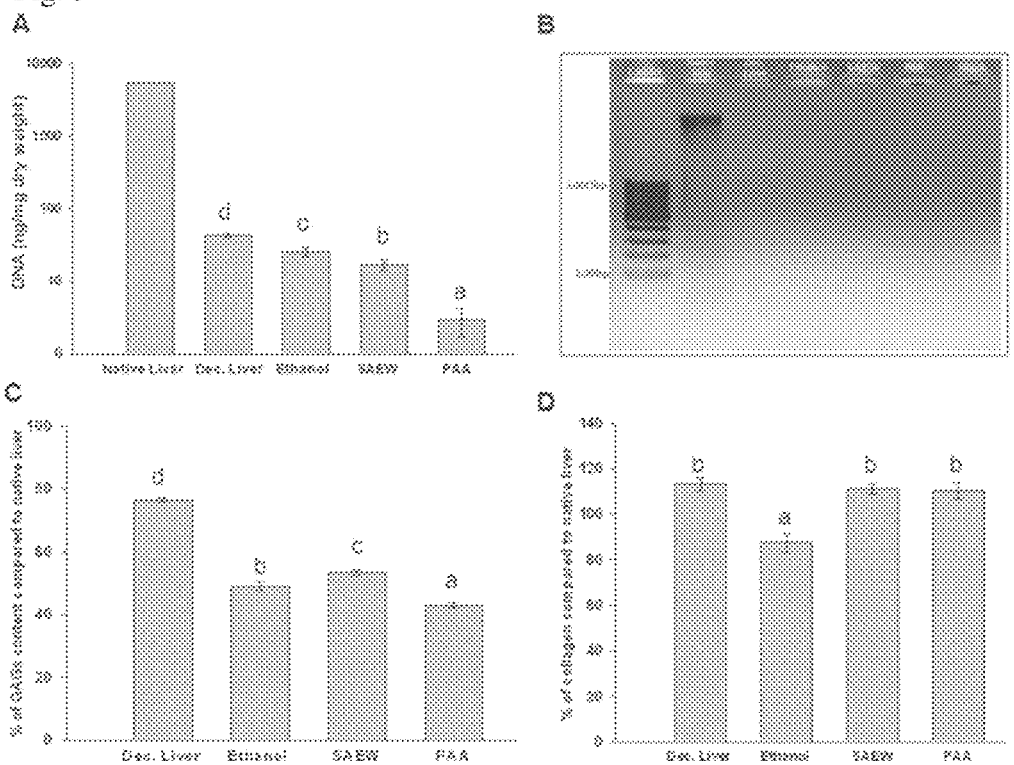
Fig. 3
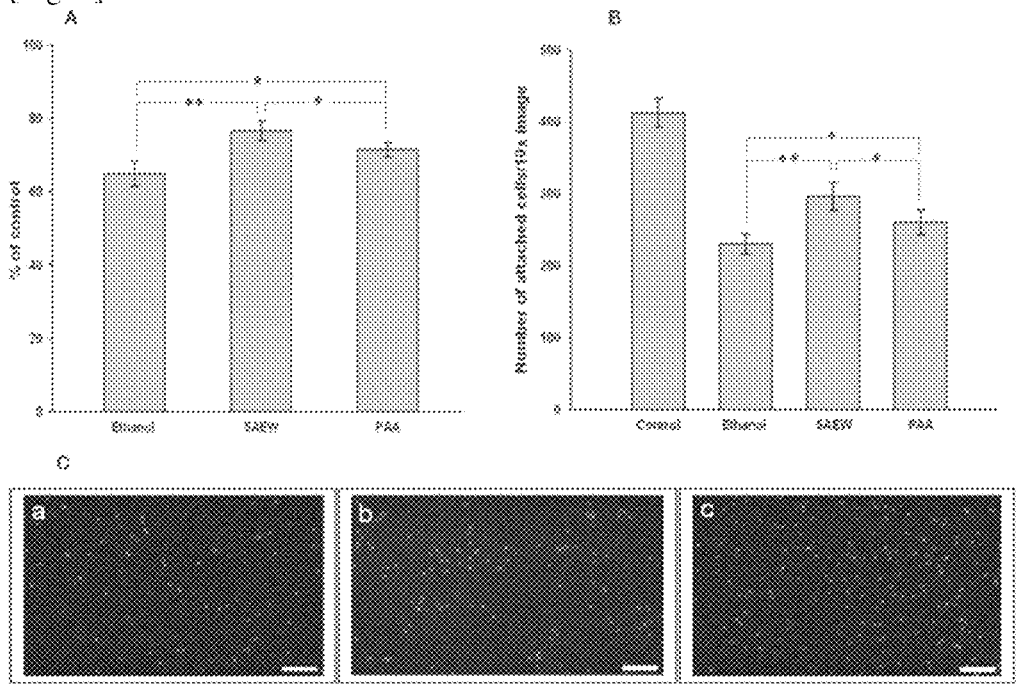
[Fig. 4]

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: 1,3 alpha gal primer F

<400> SEQUENCE: 1
gctccacctg gcagtcatag                                              20

<210> SEQ ID NO 2
<211> LENGTH: 20
<212> TYPE: DNA
<213> ORGANISM: Artificial Sequence
<220> FEATURE:
<223> OTHER INFORMATION: 1,3 alpha gal primer R

<400> SEQUENCE: 2
gtcctggagg attcccttga                                              20

```
<210> SEQ ID NO 3
<211> LENGTH: 19
<212> TYPE: DNA
<213> ORGANISM: Artificial Sequence
<220> FEATURE:
<223> OTHER INFORMATION: SLA-2 primer F

<400> SEQUENCE: 3
grcaccttga ggtgctggg                                                    19

<210> SEQ ID NO 4
<211> LENGTH: 20
<212> TYPE: DNA
<213> ORGANISM: Artificial Sequence
<220> FEATURE:
<223> OTHER INFORMATION: SLA-2 primer R

<400> SEQUENCE: 4
tggcaggtgt agctctgctc                                                   20

<210> SEQ ID NO 5
<211> LENGTH: 20
<212> TYPE: DNA
<213> ORGANISM: Artificial Sequence
<220> FEATURE:
<223> OTHER INFORMATION: SLA-DRA primer F

<400> SEQUENCE: 5
cgagaagagg tggcaagaca                                                   20

<210> SEQ ID NO 6
<211> LENGTH: 20
<212> TYPE: DNA
<213> ORGANISM: Artificial Sequence
<220> FEATURE:
<223> OTHER INFORMATION: SLA-DRA primer R

<400> SEQUENCE: 6
gtcctggagg attcccttga                                                   20

<210> SEQ ID NO 7
<211> LENGTH: 20
<212> TYPE: DNA
<213> ORGANISM: Artificial Sequence
<220> FEATURE:
<223> OTHER INFORMATION: pvWF primer F

<400> SEQUENCE: 7 gccccttttgc aggagaagat                                                  20

<210> SEQ ID NO 8
<211> LENGTH: 20
<212> TYPE: DNA
<213> ORGANISM: Artificial Sequence
<220> FEATURE:
<223> OTHER INFORMATION: pvWF primer R

<400> SEQUENCE: 8
atacagccct ttgctggcat                                                   20

<210> SEQ ID NO 9
<211> LENGTH: 20
<212> TYPE: DNA
<213> ORGANISM: Artificial Sequence
<220> FEATURE:
<223> OTHER INFORMATION: PERV primer F
```

```
<400> SEQUENCE: 9
ctaccccgag attgaggagc                                                  20

<210> SEQ ID NO 10
<211> LENGTH: 20
<212> TYPE: DNA
<213> ORGANISM: Artificial Sequence
<220> FEATURE:
<223> OTHER INFORMATION: PERV primer R

<400> SEQUENCE: 10
gggggatggt tagttttcca                                                  20

<210> SEQ ID NO 11
<211> LENGTH: 19
<212> TYPE: DNA
<213> ORGANISM: Artificial Sequence
<220> FEATURE:
<223> OTHER INFORMATION: beta-actin primer F

<400> SEQUENCE: 11
tccctggaga agagctacg                                                   19

<210> SEQ ID NO 12
<211> LENGTH: 20
<212> TYPE: DNA
<213> ORGANISM: Artificial Sequence
<220> FEATURE:
<223> OTHER INFORMATION: beta-actin primer R

<400> SEQUENCE: 12
tgttggcgta gaggtccttc                                                  20
```

COMPOSITIONS AND METHODS FOR STERILIZING BIOSCAFFOLDS

CROSS REFERENCE TO RELATED APPLICATIONS

This application is a national stage filing of PCT Application PCT/KR2013/008818 filed Oct. 2, 2013, which claims priority to Korean Patent Application No. 10-2012-0113072 filed Oct. 11, 2012, and Korean Patent Application No. 10-2012-0113110 also filed Oct. 11, 2012, all of which applications are hereby incorporated by reference herein.

TECHNICAL FIELD

The present invention relates to a composition for sterilizing a bioscaffold, comprising slightly acidic electrolyzed water (SAEW) as an active ingredient, and a method for sterilizing a bioscaffold using the same.

INTRODUCTION AND SUMMARY OF THE INVENTION

With the recent advent of aging society and the increase of various diseases and accidents, adult organ tissues run into the limits of regeneration, and the need for it increases. Therefore, extensive research on transplantable replacement organs has been conducted. Among others, a method of tissue engineering is expected to overcome immune rejection, zoonotic diseases, etc., which are side effects that may occur in xenotransplantation (animal-to-human organ transplantation) that has recently been proposed as an alternative to allotransplantation (human-to-human organ transplantation), and thus has attracted much attention in the field of regenerative medicine. In particular, as a method of tissue engineering, a bioscaffold method using decellularization has attracted much attention due to the advantages that decellularized scaffolds minimize immune rejection during transplantation, preserve extracellular matrix (ECM) involved in cell growth and differentiation, preserve vascular structure which enables the supply of oxygen and nutrients after cell injection, and retain the shape and structure of the original organs.

Meanwhile, the incidence of hepatitis B virus-related end-stage liver disease and hepatocellular carcinoma is extremely high in Asia, particularly in eastern and southeastern areas (de Villa V, Lo C M. Liver transplantation for hepatocellular carcinoma in Asia. Oncologist 2007; 12 (11):1321-1331). About 30 million people in the United States have liver disorders, with approximately 27,000 deaths reported per year due to liver disease (Uygun Be, Soto-Gutierrez A, Yagi H, et al. Oran reengineering through development of a transplantable recellularized liver graft using decellularized liver matrix. Nat Med. 2010; 16(7):814-820). Liver transplantation is the gold standard for treating patients with severe hepatic failure. However, the shortage of donors limits its application and has led to a dramatic increase in the number of patients wait-listed for liver transplantation (Punch J D, Hayes D H, LaPorte F B, McBride V, Seely M S. Organ donation and utilization in the United States, 1996-2005. Am J Transplant. 2007; 7 (5 Pt 2):1327-1338). Many studies have reported that scaffolds mimic the biological properties of the native extracellular matrix (ECM) (Lutolf M P, Hubbell J A. Synthetic biomaterials as instructive extracellular microenvironments for morphogenesis in tissue engineering. Nat Biotechnol 2005; 23(1):47-55). The scaffolds have been prepared and applied in the fields of tissue engineering and regenerative medicine. Scaffolds are composed of proteins, glycosaminoglycans (GAGs), and growth factors. A scaffold represents the ideal microenvironment and can be seeded with cells to facilitate their migration, proliferation, and differentiation (Taylor K R, Gallo R L Glycosaminoglycans and their proteoglycans: host-associated molecular patterns for initiation and modulation of inflammation. FASEB J. 2006; 20(1):9-22).

Animal-originating scaffolds must undergo treatment to minimize or eliminate the host immune response and to avoid zoonotic disease transmission after in vivo implantation in recipients (Reing J E, Brown B N, Daly K A, et al. The effect of processing methods upon mechanical and biologic properties of porcine dermal extracellular matrix scaffolds. Biomaterials. 2010; 31(33):8626-8633; Hodde J, Janis A, Hiles M. Effects of sterilization on an extracellular matrix scaffold: part ||. Bioactivity and matrix interaction. J Mater Sci Mater Med. 2007; 18(4):545-550). Many agents have been used for sterilization; however, each has disadvantages that may adversely affect ECM properties, rendering it unfit for transplantation (Brown B, Lindberg K, Reing J, Stolz D B, Badylak S F. The basement membrane component of biologic scaffolds derived from extracellular matrix. Tissue Eng. 2006; 12(3):519-526; Siritientong T, Srichana T, Aramwit P. The effect of sterilization methods on the physical properties of silk sericin scaffolds. AAPS PharmSciTech. 2011; 12(2): 771-781.; Rosario D J, Reilly G C, Ali Salah E, Glover M, Bullock A J, Macneil S. Decellularization and sterilization of porcine urinary bladder matrix for tissue engineering in the lower urinary tract. Regen Med. 2008; 3(2):145-156). Preserving GAGs, collagen, and growth factors in their natural state is highly desirable because of their critical role in the maintenance of scaffold bioactivity (Hoganson D M, Owens G E, O'Doherty E M, et al. Preserved extracellular matrix components and retained biological activity in decellularized porcine mesothelium. Biomaterials. 2010; 31(27):6934-6940; Ning L J, Zhang Y, Chen X H, et al. Preparation and characterization of decellularized tendon slices for tendon tissue engineering. J Biomed Mater Res A. 2012; 100A(6): 1448-1456). Many researchers have attempted to determine the relationship between the DNA content of scaffolds and the host immune response. They suggested that xenogenic DNA within scaffold materials plays a role in the inflammatory and tissue remodeling responses after implantation. Therefore, DNA must be effectively removed from tissues and organs (Crapo P M, Gilbert T W, Badylak S F. An overview of tissue and whole organ decellularization processes. Biomaterials. 2011; 32(12):3233-3243; Keane T J, Londono R, Turner N J, Badylak S F. Consequences of ineffective decellularization of biologic scaffolds on the host response. Biomaterials. 2012; 33(6):1771-1781). Bioscaffolds are prepared using organs of animal species other than human, particularly porcine organs, and thus there is the risk of zoonotic disease transmission from donors to recipients after implantation and the risk of occurrence of acute immune responses after implantation, which has been a major obstacle to the practical use.

Therefore, sterilization using sterilizing agents is essential to reduce or remove the immune responses in the recipients against these bioscaffolds and to prevent zoonotic disease transmission from donors to recipients after implantation.

There are various sterilizing agents. Although each agent has good sterilization/disinfection effect, the effect of removal of xenogeneic antigens is low. Moreover, the sterilizing agents affect the properties of extracellular matrix of the transplanted organ, and thus the bioscaffold cannot function as a three-dimensional culture scaffold that is highly valuable to the application plan, rendering the transplanted organ unfit for transplantation.

Specifically, ethylene oxide treatment affects the mechanical properties of extracellular matrix to cause the immune response against the bioscaffold in the host after implantation, and gamma irradiation generates free radicals with high cytotoxicity from residual lipids, causing variations in the mechanical and biological properties of extracellular matrix. Moreover, oxidants such as peracetic acid destroy glycosaminoglycans and interfere with the interactions of glycosaminoglycans with cellular growth factors, causing cell degeneration and loss of function. Electron beam irradiation causes denaturation of major proteins such as collagen, which results in extracellular matrix. Moreover, alcohol, one of the most widely used oxidants, affects the surface structure of the transplanted organ, which increases the loss of collagen, thus affecting the mechanical properties of extracellular matrix.

Meanwhile, slightly acidic electrolyzed water (SAEW), which contains free chlorine atoms, is produced by electrolysis of dilute hydrochloric acid. However, no effects of slightly acidic electrolyzed water on transplanted organs, on xenogeneic antigens of bioscaffolds, on extracellular matrices, or on sterilization of bioscaffolds are known, and there are also no studies on the slightly acidic electrolyzed water.

Therefore, the need to develop a biocompatible sterilization method, which can replace existing methods of sterilizing bioscaffolds, remove xenogeneic antigens, and does not adversely affect the properties of extracellular matrix in vivo, is urgently required.

The present inventors have studied a biocompatible sterilization method which provides a powerful sterilizing action and an excellent effect of removing immunogenic antigens and found that slightly acidic electrolyzed water (SAEW) has an excellent sterilizing effect on bioscaffolds, exhibits an excellent effect of removing immunogenic antigens, and does not adversely affect the properties of extracellular matrix in vivo, thus completing the present invention.

Therefore, the present invention provides a composition for sterilizing a bioscaffold, comprising slightly acidic electrolyzed water as an active ingredient, and a method for sterilizing a bioscaffold using the same.

The present invention provides a composition for sterilizing a bioscaffold, comprising slightly acidic electrolyzed water (SAEW) as an active ingredient.

Hereinafter, the present invention will be described in detail.

In the present invention, the term "scaffold" is used in tissue engineering and refers to any structure in which living cells are incorporated to use a combination of cells and various substances, and the term "bioscaffold" refers to a structure (scaffold) formed by decellularizing a biostructure, i.e., a living organ to remove cells and leaving the microstructures and the contour of the organ only.

The slightly acidic electrolyzed water of the present invention is also called weakly acidic electrolyzed water or slightly acidic hypochlorous acid water. The sterilization and disinfection of slightly acidic electrolyzed water is determined by the amount of free residual chlorine, which is present as $Cl_2$, hypochlorous acid (HOCl), and hypochlorite ions ($OCl^-$). Hypochlorous acid water is classified into strongly acidic hypochlorous acid water (pH of 2.7 or less, available chlorine concentration of 20 to 60 ppm) and slightly acidic hypochlorous acid water (pH of 5.0 to 6.5, available chlorine concentration of 10 to 30 ppm), and the stability of available chlorine is excellent in slightly acidic hypochlorous acid water.

The pH of the slightly acidic electrolyzed water of the present invention is 5.0 to 6.8, preferably 6.2 to 6.4. Moreover, the oxidation-reduction potential (ORP) of the slightly acidic electrolyzed water is 500 to 800 mV, preferably 780 to 797 mV.

The slightly acidic electrolyzed water according to the present invention is obtained by electrolysis of a dilute hydrochloric acid solution, during which chlorine ($Cl_2$) produced by oxidation of chloride ions ($Cl^-$) at an anode may react with $H_2O$ to produce hypochlorous acid (HOCl). The concentration of hydrochloric acid is not particularly limited, but may be 3 to 10% (v/v) of the total volume of the hydrochloric acid solution, preferably 6% (v/v).

The chlorine concentration of the slightly acidic electrolyzed water may be 5 to 50 mg/L, preferably 20 to 30 mg/L.

The bioscaffold of the present invention may be prepared from an organ of a mammal, preferably from an organ of a member of the family Canidae, a member of the family Felidae, a member of the family Suidae, a member of the family Bovidae, a member of the family Cervidae, a member of the family Giraffidae, a member of the family Tayassuidae, a member of the family Camelidae, a member of the family Hippopotamidae, a member of the family Equidae, a member of the family Tapiridae, a member of the family Rhinocerotidae, a member of the family Mustelidae, a member of the family Leporidae, a rodent, or a primate. Moreover, the organ may be a liver, a stomach, a small intestine, a large intestine, a bladder, a ureter, a heart, a pancreas, a spleen, or a kidney, preferably a scaffold prepared from a porcine liver, but not limited thereto.

The slightly acidic electrolyzed water according to the present invention has an excellent ability to sterilize the bioscaffold, and thus when the bioscaffold is immersed in the slightly acidic electrolyzed water, it is possible to eliminate pathogenic microorganisms such as bacteria, viruses, etc., with which the transplanted organ, a material source of the bioscaffold, is infected, thus preventing zoonotic disease transmission in the host after implantation (see FIG. 2).

Moreover, the slightly acidic electrolyzed water according to the present invention has an excellent ability to reduce or remove immunogenic antigens, and thus when the bioscaffold is immersed in the slightly acidic electrolyzed water, it is possible to remove immunogenic antigens, including DNA, derived from the donated organ (see FIGS. 3A and 3B).

The slightly acidic electrolyzed water according to the present invention has a little effect on extracellular matrix, such as glycosaminoglycans, collagen, etc., and thus can improve cell attachment (see FIGS. 3 C and 3D and FIG. 4).

Furthermore, the bioscaffold sterilized with the slightly acidic electrolyzed water according to the present invention has no cytotoxicity, and the sterilization with the slightly acidic electrolyzed water allows the extracellular matrix to release soluble factors that stimulate cell proliferation (see FIG. 5).

As mentioned above, the slightly acidic electrolyzed water according to the present invention has excellent effects on the sterilization of bioscaffolds and the removal of immunogenic antigens and a little effect on extracellular matrix, such as glycosaminoglycans, collagen, etc. Moreover, the scaffold sterilized with the slightly acidic electrolyzed water has excellent cell attachment and has no toxicity, and thus the slightly acidic electrolyzed water can be effectively used for the sterilization of bioscaffolds.

Moreover, the present invention provides a method for sterilizing a bioscaffold, comprising applying the composition to the bioscaffold.

In the present invention, the term "application" is a concept that includes immersion, dispersion, and spread of the bioscaffold in the composition, and coating and treatment of the bioscaffold with the composition.

The sterilization ability of the slightly acidic electrolyzed water of the present invention decreases over time, and thus it is desired to change the slightly acidic electrolyzed water every 10 to 60 minutes, preferably every 15 minutes, for maintenance of the sterilization ability. Moreover, it is preferable that the scaffold is immersed in the slightly acidic electrolyzed water for 60 minutes to 3 hours, preferably 90 minutes to 120 minutes, for complete sterilization of the bioscaffold.

The slightly acidic electrolyzed water according to the present invention has excellent effects on the sterilization of bioscaffolds and the removal of immunogenic antigens and a little effect on extracellular matrix, such as glycosaminoglycans, collagen, etc. Moreover, the scaffold sterilized with the slightly acidic electrolyzed water has excellent cell attachment and has no toxicity, and thus the slightly acidic electrolyzed water can be effectively used for the sterilization of bioscaffolds.

BRIEF DESCRIPTION OF THE DRAWINGS

FIG. 1 shows the properties of porcine liver scaffolds before and after decellularization (A: Scaffolds observed with the naked eye before decellularization; B: Scaffolds observed with the naked eye after decellularization; C: Scaffolds observed by H&E staining before decellularization; D: Scaffolds observed by H&E staining after decellularization; E: Scaffolds observed by DAPI staining before decellularization; F: Scaffolds observed by DAPI staining after decellularization; and G: PCR products observed before and after decellularization).

FIG. 2 shows the results observed with the naked eye after the porcine liver scaffolds treated with slightly acidic electrolyzed water (SAEW) according to the present invention for different times were incubated in Dulbecco's Modified Eagle's Medium (DMEM) supplemented with 10% fetal bovine serum and on Columbia blood agar medium.

FIG. 3 shows the properties of porcine liver scaffolds treated with slightly acidic electrolyzed water according to the present invention (A: DNA content; B: Result after electrophoresis of DNA; C: Glycosaminoglycan content; and D: Collagen content)

FIG. 4 shows the attachment of fibroblasts in porcine liver scaffolds treated with slightly acidic electrolyzed water according to the present invention (A: Attachment rate of fibroblasts in porcine liver scaffolds; B: Number of fibroblasts attached to porcine liver scaffolds; and C: Fibroblasts observed by DAPI staining (a: Porcine liver scaffolds treated with ethanol; b: Porcine liver scaffolds treated with peracetic acid (PAA); and c: Porcine liver scaffolds treated with slightly acidic electrolyzed water according to the present invention).

DETAILED DESCRIPTION AND EXAMPLES

Figure 5:
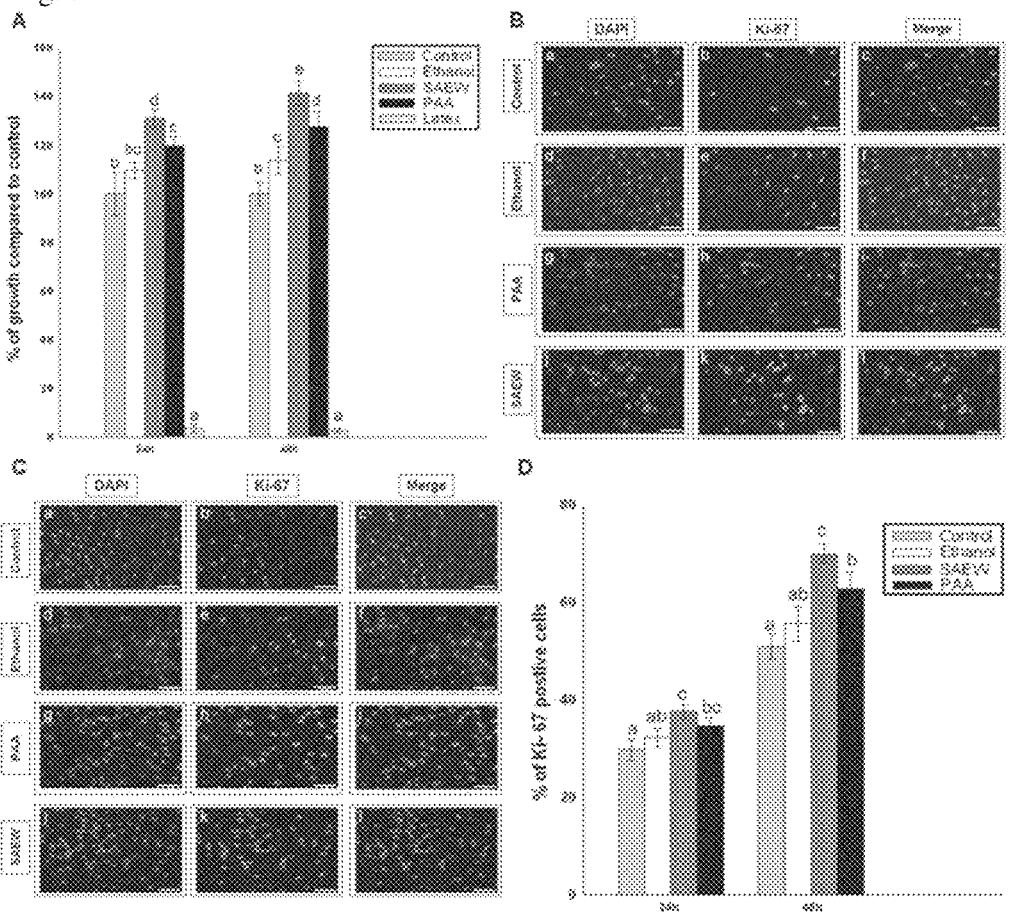
FIG. 5 shows the proliferation rate of fibroblasts in a medium in which scaffolds sterilized with slightly acidic electrolyzed water according to the present invention were incubated and the release of growth factors from scaffolds (A: Result of cytotoxicity test; B: Fibroblasts incubated with scaffolds for 24 hours and stained with anti-Ki67-antibody and DAPI; C: Fibroblasts incubated with scaffolds for 48 hours and stained with anti-Ki67-antibody and DAPI; and D: Ratio of positive cells to anti-Ki-67 antibody and DAPI).

Hereinafter, specific examples are provided to facilitate understanding of the present invention. However, the following examples are provided only for the purpose of illustrating the present invention, and the present invention is not limited by the following examples.

Example 1

Preparation and Characterization of Porcine Liver Scaffolds

1. Preparation of Porcine Liver Scaffolds

Porcine liver scaffolds were prepared as bioscaffolds to be used to determine the effects of slightly acidic electrolyzed water according to the present invention.

First, porcine livers were collected from adult crossbred pigs weighing 40 to 50 kg. Harvested liver lobes were separated and trimmed into several thin slices (2.5×1.5×0.2:0.3 cm) with a weight of 5 g per slice. Then, the slices were washed twice for 1 hour with phosphate buffered solution (PBS) containing heparin using a shaker at 120 rpm and 4° C. The slices were decellularized using 0.1% sodium dodecyl sulfate (SDS, Sigma-Aldrich) at 4° C. for 72 hours using a shaker at 120 rpm. The 0.1% SDS solutions used for decellularization were changed every 8 hours. Upon completion of decellularization, all slices were rinsed three times with PBS for 2 hours each to flush the residual SDS from the slices.

The porcine liver scaffolds before and after decellularization observed with the naked eye are shown in FIG. 1A (before decellularization) and FIG. 1B (after decellularization).

2. Characterization of Porcine Liver Scaffolds Using Hematoxylin and Eosin (H&E) Staining and DAPI Staining Livers before and after decellularization were fixed, paraffin-embedded, and sectioned according to standard protocols. Then, the liver samples were cut into 4 μm sections and stained with hematoxylin and eosin (H&E) to evaluate the efficiency of preserving the tissue architecture and removing the cellular components.

Moreover, to confirm the removal of nuclear materials, sections were also stained by DAPI staining (Vector Laboratories, Burlingame, Calif., USA).

The porcine liver scaffolds before and after decellularization observed by H&E staining are shown in FIG. 1C (before decellularization) and FIG. 1D (after decellularization). Moreover, the porcine liver scaffolds before and after decellularization observed by DAPI staining are shown in FIG. 1E (before decellularization) and FIG. 1F (after decellularization).

As shown in FIGS. 1C and 1D, unlike the native liver (before decellularization), hexagonal-shaped lobules which showed no cytoplasm and were separated by connective tissue were observed in the decellularized liver.

As shown in FIGS. 1E and 1F, the native liver showed nuclear materials, while the decellularized liver showed no nuclear materials.

3. Characterization of Porcine Liver Scaffolds by PCR Analysis

DNA was extracted from decellularized livers and native (non-decellularized) livers, and polymerase chain reaction (PCR) was performed to determine whether antigenic and pathogenic epitopes were removed by decellularization.

First, the extraction of DNA was performed using the DNeasy Blood and Tissue Kit (Qiagen, Hilden, Germany). 5 mg of lyophilized sample was digested with proteinase K buffer at 56° C. on a hot plate for 24 hours. The digest was treated with AE buffer and ethanol. DNA was eluted using AE buffer and centrifuged at 6000 rpm for 4 minutes. 50 ng of genomic DNA extracted from decellularized livers was used for PCR analysis by Tprofessional standard 96 gradient machine (Biometra, Goettingen, Germany). The PCR analysis was performed using the primers shown in Table 1. Thermal cycler conditions for amplification were the following: 94° C. for 3 minutes, followed by 34 cycles of 94° C. for 30 seconds, annealing temperature for 30 seconds, and 72° C. for 45 seconds, and a final extension at 72° C. for 10 min. PCR products were analyzed on 1% agarose gel stained with ethidium bromide. The results are shown in FIG. 1G.

3-1. Sterilization Efficiency of Slightly Acidic Electrolyzed Water on Porcine Liver Scaffolds According to Treatment Time First, the porcine liver scaffolds prepared in Example 1 were divided into two groups: an experimental group in which the scaffolds were immersed in the slightly acidic electrolyzed water prepared in Example 2 to be sterilized for minutes, 60 minutes, 90 minutes, and 120 minutes, respectively; and a control group in which the scaffolds were treated

TABLE 1

| Primer | Function | Primer sequence | Annealing Temp. | Product Size (bp) |
|---|---|---|---|---|
| 1,3 α gal | Involved hyperacute rejection after xenotransplantation | F: 5'-GCTCCACCTGGCAGTCATAG-3'<br>R: 5'-GTCCTGGAGGATTCCCTTGA-3' | 54.95 | 361 |
| SLA-2 | Involved in acute rejection | F: 5'-GRCACCTTGAGGTGCTGGG-3'<br>R: 5'-TGGCAGGTGTAGCTCTGCTC-3' | 55.04 | 185 |
| SLA-DRA | Involved in acute rejection | F: 5'-CGAGAAGAGGTGGCAAGACA-3'<br>R: 5'-GTCCTGGAGGATTCCCTTGA-3' | 54.5 | 220 |
| pvWF | Involved in thrombosis after xenotransplantation | F: 5'-GCCCCTTTGCAGGAGAAGAT-3'<br>R: 5'-ATACAGCCCTTTGCTGGCAT-3' | 60.03 | 375 |
| PERV | Involved in infection after xenotransplantation | F: 5'-CTACCCCGAGATTGAGGAGC-3'<br>R: 5'-GGGGGATGGTTAGTTTTCCA-3' | 54.9 | 317 |
| β-actin | Cell marker | F: 5'-TCCCTGGAGAAGAGCTACG-3'<br>R: 5'-TGTTGGCGTAGAGGTCCTTC-3' | 60.5 | 280 |

As shown in FIG. 1G, no genes for immunogenic and pathogenic factors that include alpha 1,3 galactosyltransferase (1,3 α gal), swine leukocyte antigen 2 (SLA-2), swine leukocyte antigen DR alpha (SLA-DRA), porcine endogenous retrovirus-gag (PERV), and porcine von Willebrand factor (pvWF) were found in the decellularized livers, and these results suggested that the scaffolds can be applied for potential xenotransplantation.

Example 2

Preparation of Slightly Acidic Electrolyzed Water (SAEW) of the Present Invention Slightly acidic electrolyzed water of the present invention was prepared according to the method described by Cao et. al (Efficiency of slightly acidic electrolyzed water for inactivation of *Salmonella enteritidis* and its contaminated shell eggs. Int J Food Microbiol. 2009; 130 (2):88-93).

First, slightly acidic electrolyzed water was prepared by placing a 6% HCl solution and a 2 M NaCl solution in an electrolysis device (Model D-7, Dolki Co. Ltd., Wonju, Korea) without a membrane and applying a current of 12 A. The pH of the prepared slightly acidic electrolyzed water was 6.2 to 6.4, the oxidation reduction potential (ORP) was 780 to 797 mV, and the chlorine concentration was 24 mg/L. The prepared slightly acidic electrolyzed water was placed into tightly sealed sterile bottles and used in the following experiment.

Example 3

Sterilization Efficiency of SAEW of the Present Invention

The following experiment was performed according to the method described by Shearer et al. to evaluate the sterilization efficiency of the slightly acidic electrolyzed water of the present invention.

with PBS, peracetic acid (PAA) solution (Sigma-Aldrich, St Louis, Mo., USA), and 70% ethanol solution (Daejung Chemicals and Metals, Seoul, Korea), instead of the slightly acidic electrolyzed water. The slightly acidic electrolyzed water was changed every 15 minutes to be the best fit for sterilization of the porcine liver scaffolds, and the sterilized porcine liver scaffolds were washed with PBS once.

The results are shown in FIG. 2.

As shown in FIG. 2, in the case of native liver (non-decellularized and untreated liver), untreated and decellularized porcine liver, and PBS-treated porcine liver scaffold, the increase in discoloration and turbidity and the formation of cell colonies were observed in both DMEM medium and blood agar medium. However, in the case of porcine liver scaffolds treated with the slightly acidic electrolyzed water of the present invention for 90 minutes and 120 minutes, respectively, the increase in discoloration or turbidity of medium was not observed, and the formation of cell colonies on blood agar medium was not observed. Therefore, it can be seen that the treatment with the slightly acidic electrolyzed water of the present invention for more than 90 minutes exhibits excellent sterilization efficiency.

3-2. Determination of the Sterilization Effect of SAEW Treatment on Scaffolds According to Culture Time The porcine liver scaffolds of the experimental group and the control group treated by the method described in the above section 3-1 were incubated in Dulbecco's Modified Eagle's Medium (DMEM; Invitrogen, Carlsbad, Calif., USA) supplemented with 10% fetal bovine serum (FBS, Hyclone, Logan, Utah, USA) at 37° C. and on Columbia blood agar medium (Fluka Chemie GmbH) for 96 hours and then checked periodically for signs of infection. In the event of infection, the discoloration and turbidity of medium increases, and the growth of cell colonies is observed on blood agar medium.

The results are shown in Table 2:

TABLE 2

| | Time (hour) | Native liver | Decellularized liver | PBS treatment | PAA treatment | Ethanol treatment | SAEW treatment |
|---|---|---|---|---|---|---|---|
| DMEM + 10% FBS | 6 | + | + | + | − | − | − |
| | 24 | x | x | x | − | − | − |
| | 36 | x | x | x | − | − | − |
| | 48 | x | x | x | − | − | − |
| | 60 | x | x | x | − | − | − |
| | 72 | x | x | x | − | + | − |
| | 96 | x | x | x | − | x | − |
| Columbia blood agar | 6 | + | + | + | − | − | − |
| | 24 | x | x | x | − | − | − |
| | 36 | x | x | x | − | − | − |
| | 48 | x | x | x | − | − | − |
| | 60 | x | x | x | − | + | − |
| | 72 | x | x | x | − | x | − |
| | 96 | x | x | x | − | x | − |

In Table 2, (−) represents that no symptoms of infection were observed; (+) represents that symptoms of infection were observed; (x) represents that symptoms of infection were observed before observation time; native liver, decellularized liver, and PBS-treated liver were used as positive controls; and medium without scaffolds was used as the negative control.

As shown in Table 2, in the case of native liver, untreated and decellularized liver, and PBS-treated liver scaffolds, the increase in discoloration and turbidity and the formation of cell colonies were observed in both DMEM medium and blood agar medium. Moreover, in the case of ethanol-treated porcine liver scaffolds, the growth of cells cultured on Columbia blood agar medium for 60 hours was observed, and the discoloration of cells cultured in DMEM for 72 hours was observed.

However, in the case of porcine liver scaffolds treated with the slightly acidic electrolyzed water of the present invention and PAA, the increase in discoloration or turbidity of medium was not observed, and the formation of cell colonies on blood agar medium was also not observed. Therefore, it can be seen that the treatment with the slightly acidic electrolyzed water of the present invention exhibits excellent sterilization efficiency.

Example 4

Determination of the Effect of SAEW of the Present Invention on Scaffolds 4-1. The Effect of SAEW of the Present Invention on the Removal of Immunogenic Antigens The following experiment was performed to evaluate the effects of the slightly acidic electrolyzed water of the present invention on the removal of immunogenic antigens.

First, lyophilized samples of native porcine liver slices, scaffolds decellularized by the method of Example 1, porcine liver scaffolds treated with 0.1% peracetic acid solution (PAA; Sigma-Aldrich, St Louis, Mo., USA), PBS, 70% ethanol (Daejung Chemicals and Metals, Seoul, Korea), and slightly acidic electrolyzed water were prepared. Then, DNA was extracted from the lyophilized samples using the DNeasy Blood and Tissue Kit (Qiagen, Hilden, Germany).

Equal amount of extracted DNA were separated by electrophoresis on a 1% agarose gel containing 0.5% ethidium bromide and visualized by ultraviolet transillumination to determine residual DNA fragment size. At this time, a reference 100-base pair DNA ladder (GeneRuler 100 bp plus DNA ladder, Fermentas) was used as a marker to determine the DNA fragment size.

The results are shown in FIG. 3.

As shown in FIG. 3, the DNA content in (decellularized) scaffolds treated with the slightly acidic electrolyzed water of the present invention was significantly lower (16.85±0.74 ng/mg) compared to the control group treated with PBS (32.11±2.88 ng/mg) or ethanol (25.7±3.63 ng/mg) (FIG. 3A). The DNA content in untreated scaffolds was 42.5±3.21 ng/ml, and thus it was confirmed that the efficiency of the slightly acidic electrolyzed water of the present invention for removing the DNA content was 60.29±6.68% (in the case of PAA treatment, the DNA content was 2.9±1.20 ng/mg, and the efficiency for removing the DNA was 93.13±2.82%).

Moreover, in the electrophoresis, the untreated liver scaffolds showed a distinct apparent DNA band at 1500 base pairs or larger, whereas the SAEW-treated scaffolds showed no DNA band (FIG. 3B).

Therefore, the slightly acidic electrolyzed water of the present invention has an excellent effect of removing the DNA of bacteria, viruses, etc. which are highly likely to remain in the scaffold, as well as the DNA of cells of the donated organ remaining in the scaffold, which act clinically as immunogenic antigens, and thus can effectively used in the sterilization method for sterilizing bioscaffolds and removing immunogenic antigens.

4-2. The Effect of SAEW of the Present Invention on Glycosaminoglycan Content

To evaluate the effects of the slightly acidic electrolyzed water of the present invention on the content of glycosaminoglycans, the content of glycosaminoglycans in decellularized liver (untreated scaffolds), scaffolds treated with PBS, and scaffolds treated with the slightly acidic electrolyzed water of the present invention were determined using a dimethyl methylene blue dye-binding assay kit (Blyscan kit; Biocolor Ltd) according to the manufacturer's instructions. First, 5 mg of lyophilized sample was homogenized and solubilized. A 100 μL aliquot from each sample lysate was added to 1 mL of dimethyl methylene blue solution and agitated on a shaker at 25° C. for 30 minutes. The resulting solutions were then centrifuged at 10,000×g for 10 minutes to collect the GAG dye complex, and the supernatants were discarded. The remaining pellet was suspended in 1 mL of the provided dissociation reagent, and the absorbance was measured at 655 nm. Chondroitin sulfate provided in the kit was used as a standard of glycosaminoglycans.

The results are shown in FIG. 3C.

As shown in FIG. 3C, it can be seen that the content of glycosaminoglycans in scaffold treated with PAA was 43±0.80% of that in untreated scaffolds and 56±1.04% of that in untreated and decellularized scaffolds. Moreover, it can be seen that the content of glycosaminoglycans in scaffold treated with PBS was 68.7±0.320% of that in untreated scaffolds and 89.8±0.418% of that in untreated and decellularized scaffolds. Furthermore, it can be seen that the content of glycosaminoglycans in scaffold treated with ethanol was 49.1±1.47% of that in untreated scaffolds and 64.16±1.92% of that in untreated and decellularized scaffolds.

Contrary to this, the content of glycosaminoglycans in scaffolds treated with the slightly acidic electrolyzed water of the present invention was 53.3±0.83% of that in untreated scaffolds and 69.6±0.58% of that in untreated and decellularized scaffolds.

Glycosaminoglycans are already known to play a critical role of preserving growth factors and cytokines which are essential for the growth, proliferation, and differentiation of cells, and thus when the bioscaffold is sterilized with the slightly acidic electrolyzed water of the present invention, it does not affect the properties of extracellular matrix, such as growth factors and cytokines, compared to other sterilizing agents, thus obtaining sterilization effect while maintaining cell attachment.

4-3. The Effect of SAEW of the Present Invention on Collagen Content

To evaluate the effects of the slightly acidic electrolyzed water of the present invention on the content of collagen, the total collagen levels in native liver, decellularized scaffolds (untreated), scaffolds treated with PBS, PAA, or ethanol, and scaffolds treated with the slightly acidic electrolyzed water of the present invention were determined using a Sircol collagen dye-binding assay kit (Biocolor Ltd.) according to the manufacturer's instructions.

In more detail, lyophilized samples of native porcine liver slices, scaffolds decellularized by the method of Example 1, porcine liver scaffolds treated with PAA, PBS, ethanol, and slightly acidic electrolyzed water, respectively, were prepared. Then, total acid pepsin-soluble collagen was obtained after incubation in 0.5 M acetic acid containing 0.1 mg/ml pepsin. A 100 µL aliquot of acid neutralizing reagent was added to the acid-pepsin extract. Then, the extract was centrifuged after an overnight incubation at 4° C. Then, 1 mL Sircol dye reagent was added to the pellet and incubated at 25° C. for 30 minutes. After centrifugation, the pellet was washed with acid-salt wash reagent and suspended in 1 mL of alkaline reagent. Then, the absorbance was measured at 540 nm. The results are shown in FIG. 3D.

As shown in FIG. 3D, it can be seen that the content of collagen in scaffolds treated with the slightly acidic electrolyzed water of the present invention was 111.13±2.19% of that in native liver. The increase in the content of collagen in scaffolds treated with slightly acidic electrolyzed water suggests that large amount of cellular proteins were removed from the scaffolds.

Compared to this, the content of collagen in scaffolds treated with ethanol was 87.54±4.07% of that in native liver.

It can be seen from the above results that ethanol, one of the existing sterilizing agents, affects the collagen in bioscaffolds, but the slightly acidic electrolyzed water of the present invention does not affect the content of collagen in bioscaffolds.

Example 5

The Effect of SAEW of the Present Invention on Cell Attachment of Bioscaffolds

The following experiment was performed to evaluate the effects of the slightly acidic electrolyzed water of the present invention on the cell attachment and viability.

First, small discs of porcine liver scaffolds treated with slightly acidic electrolyzed water and different sterilizing agents (PAA, ethanol) were placed into a 96-well plate, and fibroblasts were harvested from tissue culture dishes, counted, and resuspended in complete DMEM containing 10% fetal bovine serum (FBS). Then, a 100 µL aliquot of DMEM in which porcine fibroblasts were suspended was added to each scaffold disc such that a total of about 50,000 fibroblasts were seeded on the plates. Then, the plate was incubated at 37° C. in 5% $CO_2$ atmosphere for 3 hours to allow the fibroblasts to attach to scaffold substrates. The scaffold substrates were carefully transferred to another well such that the cells attached to the scaffold would remain undisturbed. Then, the plate was incubated at 37° C. in 5% $CO_2$ atmosphere for 12 hours. Then, 10 µL of MTT solution (3-[4,5-dimethylthiazol-2yl]-2,5-diphenyltetrazolium bromide; 5 mg/ml, Sigma Aldrich) dissolved in PBS was added to each well and incubated at 37° C. in 5% $CO_2$ atmosphere for 5 hours. Then, the media were removed and 200 µL of dimethyl sulfoxide (DMSO) was added to each well to dissolve the formazan by pipetting. After incubation for 10 minutes, 100 µL of solutions from the respective substrate wells were pipetted into another 96-well plate. Finally, the absorbance of the samples was determined using a spectrophotometer with a test wavelength of 570 nm and a reference wavelength of 630 nm.

Moreover, DAPI (4',6-diamidino-2-phenylindole; Sigma-Aldrich, St Louis, Mo., USA)-labeled porcine fibroblasts were incubated in the same manner for 16 hours. Then, the scaffolds were checked by phase-contrast fluorescence inverted microscopy (Olympus, Tokyo, Japan) to count the number of attached cells. The number of DAPI-labeled cells was counted using Image J software (National Institutes of Health, Bethesda, Md., USA).

The percentage of seeded fibroblasts attached to the scaffold substrate and remained metabolically active is shown in FIG. 4A, the number of attached cells is shown in FIG. 4B, and the fibroblasts stained with DAPI (4',6-diamidino-2-phenylindole; Sigma Aldrich, St Louis, Mo., USA) are shown in FIG. 4C.

As shown in FIG. 4A, the MTT cell attachment assay revealed that 76.65±2.66% of the porcine fibroblasts seeded on scaffolds sterilized with slightly acidic electrolyzed water and incubated for 3 hours were attached and remained viable for 16 hours. Compared to this, 64.86±3.48% and 71.50±1.95% of seeded fibroblasts were attached to the scaffolds treated with ethanol and PAA, respectively (FIG. 4A).

The above results suggest that the attached cells interacted with the extracellular matrix in the scaffolds.

Moreover, as shown in FIGS. 4B and 4C, an evaluation of the number of DAPI-labeled fibroblasts using phase-contrast fluorescence inverted microscopy confirmed that the number of fibroblasts attached to scaffolds treated with slightly acidic electrolyzed water was higher than that in scaffolds treated with PAA or ethanol, indicating that the cell attachment and viability are excellent.

Therefore, when the slightly acidic electrolyzed water of the present invention is used in the sterilization of scaffolds, it promotes the interaction of cells seeded in scaffolds with the extracellular matrix in the scaffolds to increase the cell attachment and viability and thus can be effectively used in the sterilization for increasing cell attachment.

Example 6

Analysis of Cytotoxicity of Bioscaffolds Sterilized with of SAEW of the Present Invention and Determination of Release of Soluble Factors that Stimulate Cell Proliferation 6-1. Analysis of Cytotoxicity of Bioscaffolds Sterilized with of SAEW of the Present Invention The following experiment was performed to evaluate the cytotoxicity of bioscaffold treated with the slightly acidic electrolyzed water of the present invention.

Conditioned cell culture media were prepared from scaffolds treated with the slightly acidic electrolyzed water of the present invention. In brief, serum-free DMEM cell culture medium was incubated overnight with each SAEW-treated scaffold at a concentration of 0.2 g/ml media at 37° C. in a shaker at 70 rpm/min. Cell culture media without scaffolds were prepared by the same method as above to provide unconditioned controls. After incubation, the scaffolds were removed and the medium was filtered through a 0.4 μm filter to prepare culture medium containing soluble factors released from extracellular matrix.

Then, porcine skin fibroblasts were harvested from tissue culture dishes, counted, and resuspended in complete DMEM containing 10% FBS. Then, a 100 μL aliquot of DMEM in which porcine fibroblasts were suspended was added to each scaffold disc such that a total of about 10,000 fibroblasts were seeded on each well. Then, the plate was incubated at 37° C. in 5% $CO_2$ atmosphere for 24 hours to allow the fibroblasts to attach to the well.

The medium in which fibroblasts were incubated was aspirated, followed by the addition of conditioned or unconditioned culture medium containing 10% FBS and 1% penicillin-streptomycin (Gibco, Grand Island, N.Y., USA) to the well with attached fibroblasts, and the plate was incubated 37° C. in 5% $CO_2$ atmosphere for 24 hours and 48 hours (the culture medium was changed every 24 hours). After 24 hours, 10 μL of MTT solution (5 mg/ml in PBS) was added to each well, pipetted, and incubated at 37° C. in 5% $CO_2$ atmosphere for 4 hours. Then, the media were removed and 200 μL of DMSO was added to each well to dissolve the formazan by pipetting. Finally, the absorbance of the samples was determined using a spectrophotometer with a test wavelength of 570 nm and a reference wavelength of 630 nm.

The results are shown in FIG. 5A.

As shown in FIG. 5A, the conditioned medium prepared from scaffolds treated with the slightly acidic electrolyzed water showed higher cell proliferation of fibroblasts than the unconditioned medium.

In detail, it was found that the proliferation rate of fibroblasts in the medium prepared from scaffolds treated with the slightly acidic electrolyzed water was 131.29±5.49% (after incubation for 24 hours) and 141.46±4.78% (after incubation for 48 hours) compared to that of the unconditioned medium (PAA treatment: 119.18±5.6% (after incubation for 24 hours) and 127.43±6.68% (after incubation for 48 hours); ethanol treatment: 109.22±5.58% (after incubation for 24 hours) and 113.95±6.67% (after incubation for 48 hours)).

The above results suggest that the extracellular matrix release soluble factors that stimulate the proliferation of fibroblasts and the culture medium in which scaffolds sterilized with the slightly acidic electrolyzed water were incubated has no growth inhibitory effect on fibroblasts.

6-2. Determination of Release of Soluble Factors that Stimulate Cell Proliferation of Bioscaffolds Sterilized with SAEW of the Present Invention The following experiment was performed to evaluate the ability of scaffolds prepared in the above manner, from which the cytotoxicity that might result from slightly acidic electrolyzed water remaining in the scaffolds (decellularized liver tissue) was excluded by sterilization, to release soluble factors that stimulate biological viability.

Conditioned and control media were prepared by the method described in Example 6-1, and about 5000 porcine fibroblasts were cultured on gelatin-coated 4-well plates for 24 hours. Then, the medium was switched to conditioned or control medium. The medium was changed every 24 hours. The proliferation potential of the soluble factors eluted from the scaffolds was checked after incubation for 24 hour and 48 hours. Cells were immunostained using anti-Ki-67 antibody (Abcam, Cambridge, UK). Texas Red goat anti-rabbit IgG (Invitrogen) was used as a secondary antibody. Nuclei were counterstained using a mounting medium containing DAPI. The percentage of Ki-67 positive cells was calculated as the ratio of average positive Ki-67 cells relative to 250 DAPI-stained cells.

The results are shown in FIGS. 5B to 5D.

As shown in FIGS. 5B to 5D, it was found the percentage of Ki-67 positive cells was significantly higher in fibroblasts cultured in conditioned media prepared from scaffolds treated with the slightly acidic electrolyzed water for 24 hours (37.6±1.45%) or 48 hours (70.2±1.33%). Moreover, no significant difference was observed in conditioned media prepared from the ethanol-treated scaffolds or PAA-treated scaffolds compared to the control group.

It can be seen that the scaffolds prepared in the above manner, from which the cytotoxicity that might result from slightly acidic electrolyzed water remaining in the scaffolds (decellularized liver tissue) is excluded by sterilization, can release soluble factors that stimulate biological viability.

The invention claimed is:

1. A method for sterilizing a bioscaffold, the method comprising applying a composition for sterilizing a bioscaffold comprising slightly acidic electrolyzed water (SAEW) as an active ingredient to a bioscaffold.

2. The method of claim 1, wherein the application comprises at least one member selected from the group consisting of immersion, dispersion, spread, and coating.

3. The method of claim 2, wherein the immersion is performed for 60 minutes to 3 hours.

4. The method of claim 1, wherein the slightly acidic electrolyzed water is changed every 10 to 60 minutes.

5. The method of claim 1, wherein the slightly acidic electrolyzed water removes immunogenic antigens of the bioscaffold or increases cell attachment to the bioscaffold.

* * * * *